United States Patent [19]

Hope

[11] Patent Number: Plant 5,927

[45] Date of Patent: Apr. 7, 1987

[54] KALANCHOE PLANT NAMED VERACRUZ

[75] Inventor: Claude Hope, Cartago, Costa Rica

[73] Assignee: Ball Pan Am Plant Company, Parrish, Fla.

[21] Appl. No.: 745,129

[22] Filed: Jun. 17, 1985

[51] Int. Cl.[4] ..... A01H 5/00

[52] U.S. Cl. ..... Plt./68

[58] Field of Search ..... Plt./66

[56] References Cited

U.S. PATENT DOCUMENTS

P.P. 4,567 7/1980 Hope ..... Plt./68

*Primary Examiner*—James R. Feyrer

*Attorney, Agent, or Firm*—Schwartz, Jeffery, Schwaab, Mack, Blumenthal & Evans

[57] ABSTRACT

A new and distinct cultivar of Kalanchoe plant named Veracruz, characterized by its salmon pink flower color, compact and free branching habit, floriferous habit, 12 week flowering response, small, thick leaves, and by its suitability for production in 10–15 cm pots.

1 Drawing Figure

1

The present invention relates to a new and distinct cultivar of Kalanchoe plant, botanically known as Kalanchoe, and referred to by the cultivar name Veracruz.

The new cultivar was referred to during the breeding and selection process by the designation KLV80-11-P, and is a product of a planned breeding program. The basic objective of the breeding program was to create a new Kalanchoe cultivar having intense pink flowers, compact habit, early flowering, and good keeping qualities.

The new cultivar was originated from a cross made by Claude Hope in a controlled breeding program in Linda Vista, S.A., Cortago, Costa Rica. The female and male parents cannot be verified at this time.

Veracruz was discovered and selected by me as a flowering in a controlled environment in Linda Vista, S.A., Cortago, Costa Rica. Asexual reproduction of the new cultivar by stem cuttings, as performed by me at Cortago, Costa Rica, and by Ball Pan Am Plant Co. at Parrish, Fla., has demonstrated that the combination of characteristics as herein disclosed for the new cultivar are firmly fixed and are retained through successive generations of asexual reproduction.

Veracruz has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Veracruz, which in combination distinguish this Kalanchoe as a new and distinct cultivar;

1. Bright salmon pink flower color.
2. Compact habit and average growth rate.
3. Freely branching, with shoots formed at every node.
4. Suitable for production in 10 to 15 cm pots.
5. Flowering in 12 weeks using photoperiodic control.
6. Very floriferous, with numerous flowers formed at every shoot.
7. Responds to B-9 applications to control height.

2

8. Small leaves that are very thick and persistent.

The new cultivar is most similar to Tijuana, disclosed in my pending Application Ser. No. 54,488, filed Mar. 27, 1984. Veracruz is principally distinguished from Tijuana by its salmon pink flower color and its narrower leaves.

The accompanying photographic drawing shows a typical specimen plant of the new cultivar. The photograph is in black and white except for a cluster of flowers which represent the true flower color of Veracruz.

In the following description, color references are made to The Royal Horticultural Society Colour Chart (RHS), except where general terms of ordinary significance are used. Color values were taken under inflorescent light conditions in Bradenton, Fla.

Botanical classification: Kalanchoe, cv. Veracruz.

Propagation: The new cultivar holds its distinguishing characteristics through successive propagations by leaf cuttings and by division of shoots.

(A) *Type cutting.*—Shoot tip.

(B) *Time to root.*—10–14 days at 20° C.

(C) *Rooting habit.*—Fibrous; many very fine roots.

Plant description:

(A) *Form.*—Upright, short compact growth; scheduling practices can produce small plants in 10 cm pots or large plants in 15 cm pots.

(B) *Habit of growth.*—Average rate for this type of plant; shoots are formed at every node; freely branching.

(C) *Foliage.*—Leaves simple, opposite and elliptical, with serrated to repand margins. (1) Size: 1"–3.5" long; 1.5"–1.75" wide depending on culture. (2) Shape: Elliptical. (3) Texture: Smooth and waxy, succulent. (4) Margin: Serrate to repand. (5) Color: Young foliage, top side 147A, under side, 147B. Mature foliage top side 147A, under side 147B.

Flowering description:

(A) *Flowering habits.*—Very floriferous.

(B) *Natural flowering season.*—Fall. Flowering time under controlled daylength at 70° F. in summer is 12 weeks; in winter at 70°, 14 weeks. Flowering time depends on temperature, light intensity and other growing conditions.

(C) *Flower buds.*—Oblong, developing to tubulus as petals mature. Sheathed with four green sepals. (1) Size: ½". (2) Rate of opening: Normal.

(D) *Flowers borne.*—On compound dichasial cyme on strong peduncles; peduncle length depends on growing conditions and B-9 applications; pedicels up to 2 mm long.

(E) *Quantity of flowers.*—Very floriferous, with new buds continuing to develop.

(F) *Petals.*—(1) Shape: Peltate, tip cuspidate. (2) Color: Top side when opening 52A–52C, fading to 52D; (3) Number and size of petals: Four, united in the corolla; petals ⅛" in diameter; total flower diameter ½".

(G) *Reproductive organs.*—(1) Stamens: 8 in number. (a) Anther shape: Flat, elliptical. (b) Filament color: Yellow. (c) Pollen color: Yellow. (2) Pistils: (a) Stigma: Flat, crystalline. (b) Styles: Greenish white. (c) Ovaries: 4 celled, approximately 7 mm long; green.

Disease resistance: No known Kalanchoe diseases observed to date.

I claim:

1. A new and distinct cultivar of Kalanchoe plant named Veracruz, as illustrated and described, and particularly characterized by its salmon pink flower color, compact and free branching habit, floriferous habit, 12 week flowering response, small, thick leaves, and by its suitability for production in 10–15 cm pots.

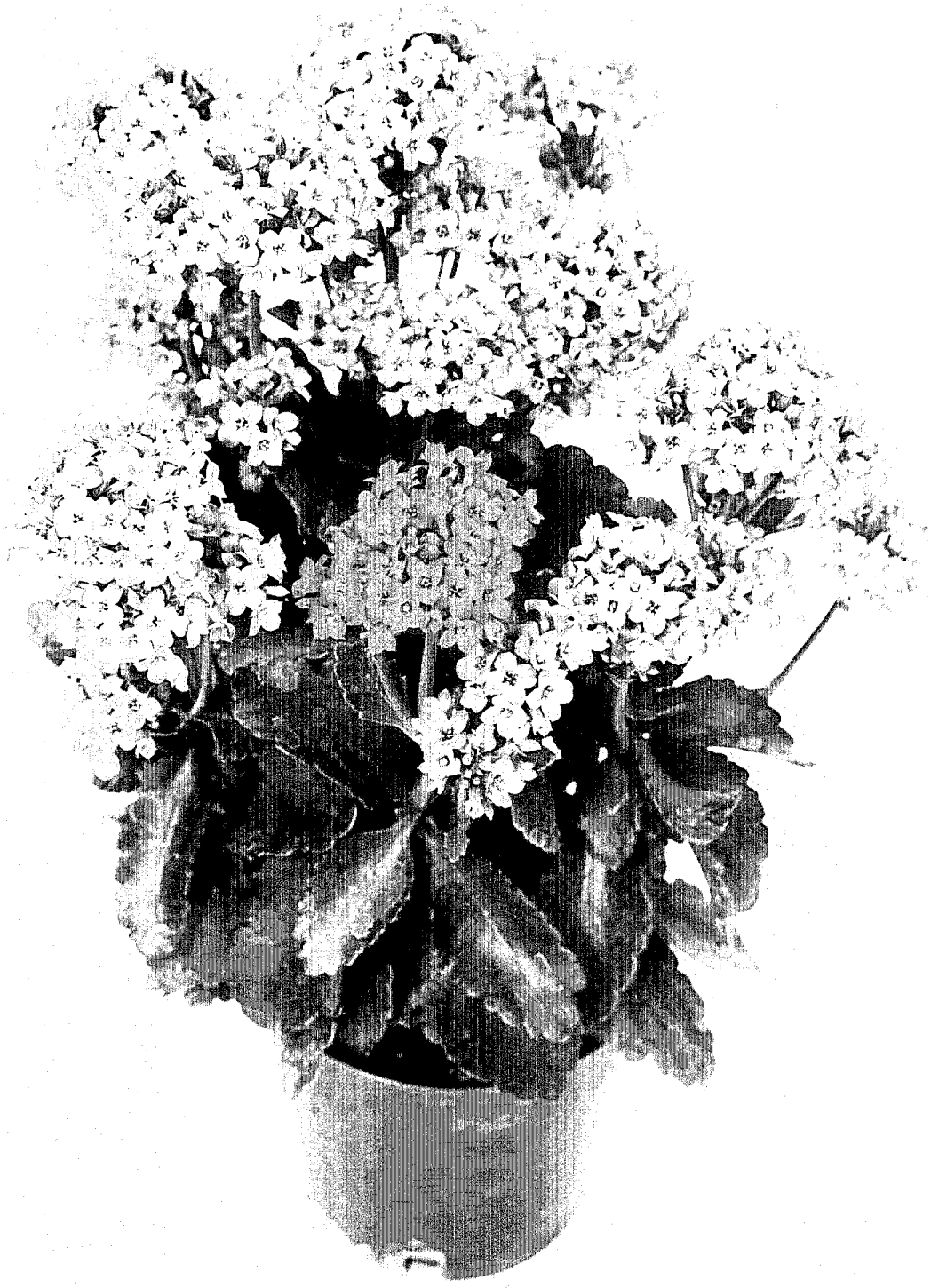

* * * * *